United States Patent [19]

Hayashi

[11] Patent Number: 6,028,132

[45] Date of Patent: Feb. 22, 2000

[54] ANTISTATIC AGENTS, COATINGS AND ADHESIVES

[75] Inventor: Kanji Hayashi, Tokyo, Japan

[73] Assignee: Altech Company Limited, Tokyo, Japan

[21] Appl. No.: 09/063,807

[22] Filed: Apr. 21, 1998

[30] Foreign Application Priority Data

Apr. 22, 1997 [JP] Japan ................................. 9-104868

[51] Int. Cl.⁷ ............................. C08K 5/06; C08F 18/22; C08G 18/28

[52] U.S. Cl. ......................... 524/247; 524/755; 524/766; 525/328.4; 525/351; 525/378; 528/71

[58] Field of Search ................................. 524/247, 755, 524/766; 525/328.4, 351, 378; 528/71

[56] References Cited

U.S. PATENT DOCUMENTS 4,238,878 12/1980 Markusch et al. ..................... 528/67
5,124,381 6/1992 Ward ..................................... 524/114

*Primary Examiner*—Kriellion Sanders
*Attorney, Agent, or Firm*—McGlew and Tuttle, P.C.

[57] ABSTRACT

Antistatic agents, adhesives and coatings with high antistatic properties under low humidity and temperature, which contain a quaternary ammonium salt of formula I:

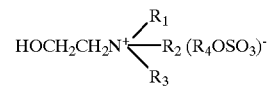

wherein each of $R_1$, $R_2$ and $R_3$ is an alkyl radical having 1–5 carbon atoms, and $R_4$ is an alkyl radical having 1–3 carbon atoms.

7 Claims, No Drawings

ANTISTATIC AGENTS, COATINGS AND ADHESIVES

BACKGROUND OF THE INVENTION

1. Field of the Invention

The present invention relates to antistatic agents, coatings, and adhesives which can be used in the production of various industrial materials such as melt or sublimation type thermal transfer ink ribbons and laminated packaging materials. The antistatic properties of these materials are significantly maintained without reducing their antistatic induction properties under low ambient temperature, especially when used as adhesive primers for plastic film or as adhesives.

2. Description of the Prior Art

The mainstream antistatic materials in current use are surfactants, and their antistatic property depends largely on the ion electroconductivity that is generated by moisture intervention. Since ion electroconductivity decreases under low ambient humidity, the quantity of antistatic agents used as antistatic measures must be adjusted to reflect changes in humidity, such as different humidity levels (% relative humidity, RH) in winter (low humidity) and summer (high humidity).

Currently used antistatic agents present different problems. The problem of using surfactants as antistatic agents lies in their bleed effects, as large usage of surfactants interferes with the adhesive strength of a given laminated film. While it is more desirable to use polymer type antistatic agents, their antistatic property also depends on ion electroconductivity, and they are thus susceptible to low ambient humidity as well. The present invention aims at solving these problems.

SUMMARY OF THE INVENTION

It is among the objects of the present invention to provide a substance possessing the property of an ion carrier preventing the decrease of ion conductivity of antistatic materials.

It has been found according to the present invention that an antistatic agent for a coating or adhesive composition may be provided, comprising a polymer type resinous material containing a quaternary ammonium salt of formula I:

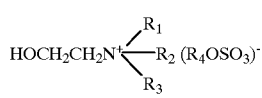

I wherein each of $R_1$, $R_2$ and $R_3$ is an alkyl radical having 1–5 carbon atoms, and $R_4$ is an alkyl radical having 1–3, especially 1–2, carbon atoms. This salt may be designated tri($C_1$–$C_5$ alkyl) (2-hydroxyethyl) ($C_1$–$C_3$ alkyl) ammonium sulfate.

According to a first aspect of the present invention, an antistatic coating or adhesive composition is provided, which comprises a resinous material selected from the group consisting of a water soluble polymer type resinous material and an aqueous emulsion polymer type resinous material, the resinous material containing a quaternary ammonium salt of formula I.

According to a second aspect of the present invention, an antistatic coating or adhesive composition is provided, which comprises a polyester type resinous material which is soluble in an organic solvent, such as ketones, esters and alcohols, the resinous material containing a quaternary ammonium salt of formula I.

The present invention also contemplates a method of using a quaternary ammonium salt of formula I, which comprises adding the quaternary ammonium salt to a polymer type resinous material for providing an antistatic coating or adhesive composition. The resinous material may be that contemplated per the first or second aspect of the invention as noted above.

In particular, per the first aspect of the invention, the quaternary ammonium salt may be reacted with an acrylic copolymer to form a polymer type antistatic adhesive primer, and per the second aspect of the invention, the quaternary ammonium salt may be reacted with a polyisocyanate in a polyether polyol resinous solvent.

The various features of novelty which characterize the invention are pointed out with particularity in the claims annexed to and forming a part of this disclosure. For a better understanding of the invention, its operating advantages and specific objects attained by its uses, reference is made to the accompanying descriptive matter and examples in which preferred embodiments of the invention are illustrated.

DETAILED DESCRIPTION OF THE INVENTION

This invention mitigates potential problems caused by static electricity without reducing the antistatic conductivity properties of polymer resin products under low ambient humidity.

When an acrylic copolymer possessing a quaternary ammonium base is used on the chemical chain as a polymer type antistatic adhesive primer, the surface resistivity of the primer under 50–60% (high) ambient humidity is $10^8$–$10^{10} \Omega/cm^2$, reflecting a sufficient antistatic property. However, the surface resistivity increases to $10^{11}$–$10^{13} \Omega/cm^2$ under 15–20% (low) ambient humidity, showing a tendency to decrease the antistatic property considerably. This problem occurs particularly during periods of lower humidity such as in winter.

This decrease of antistatic property, however, is not only caused by low humidity. An increase of surface resistivity due to the free movement of the polymer in molecular space can also be observed with the polymer type antistatic agents exposed under low temperature conditions.

The decrease of antistatic performance under low ambient temperature and humidity can be solved by adding the quaternary ammonium salt of formula I to the above adhesive primer compounds per the first aspect of the invention. This method can be applied not only to the adhesive primer compounds but also to the adhesive compounds per the second aspect of the invention with similar effects.

An effective antistatic performance of plastic laminated film under low ambient humidity can be obtained with the adhesive agents per the second aspect of the invention reacting with polyisocyanate through the addition of the quaternary ammonium salt of formula I to a polyether polyol resinous solvent. This is especially true with urethane type adhesives.

The chemical compound of formula I can also be added to the binder of a printing ink or to the medium component to provide a simple mixture thereof for improving the antistatic performance of the printing ink.

Combining the acrylic (including methacrylic) acid ester of the chemical compound of formula I with an acrylic copolymer creates a highly heat resistant antistatic polymer. Heat resistant antistatic coatings capable of retaining their antistatic quality under exposure to 150° C. temperature for a period of 60 minutes, can be created with the combined components of this polymer and an epoxy compound (crosslinker). However, this polymer is basically ion electroconductive also, and its antistatic property decreases under low ambient humidity. In this case, the decrease of antistatic performance under low ambient humidity can be prevented by adding the chemical compound of formula I to the above polymer components.

Thus, according to the present invention, the quaternary ammonium salt of formula I constitutes a substance possessing the property of an ion carrier preventing the decrease of ion conductivity of antistatic materials.

The quaternary ammonium salt of formula I can be created through alkyl sulfonation of dimethylamino ethanol with dialkyl sulfate, e.g. with cooling of the attendant exothermic reaction. The quaternary ammonium compounds of this invention preferably contemplate dimethylsulfate or diethylsulfate type compounds having the formulas Ia and Ib, respectively:

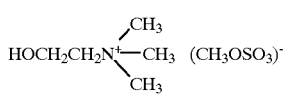

Ia which may be designated trimethyl (2-hydroxyethyl) methyl ammonium sulfate, and

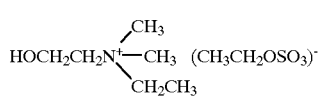

Ib which may be designated ethyldimethyl (2-hydroxyethyl) ethyl ammonium sulfate.

The acrylic (including methacrylic) acid ester of these quaternary ammonium compounds, such as

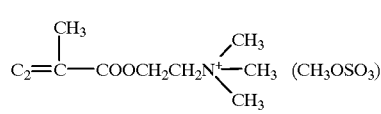

Ia-1 which may be designated trimethyl (2-methylacryloyloxyethyl) methyl yammonium sulfate (DQS), i.e. the corresponding methacrylic acid ester of the salt of formula Ia, is effective as a comonomer of antistatic acrylic copolymers, and their copolymers are extremely useful as main components of the above described heat resistant antistatic adhesive primer. Addition of a quaternary ammonium salt of formula Ib to this adhesive primer is especially effective against low humidity.

Furthermore, antistatic adhesive agents for dry laminates, previously unavailable, can now be achieved by reacting the terminal of this quaternary ammonium compound, e.g. the methacrylate monomer DQS of formula Ia-1, with the OH base and isocyanate NCO base (i.e. OH+NCO—→NHCOO—) at ordinary temperature or with heating to decrease the reaction time. The structure and properties thereof are explained hereunder with some examples.

EXAMPLES

The following examples are given by way of illustration and not limitation of the present invention. As used herein, all parts and percentages (%) are by weight unless otherwise indicated.

Example 1

Coatings with excellent antistatic and heat resistant properties were achieved with components whose main constituent is a 30% solution of the below stated acrylic polymer in isopropyl alcohol (IPA)/water base (1/1) mixed solvent. This coating material is an acrylic copolymer (30% solution) consisting of the methacrylate monomer of the salt of formula Ia-1 (DQS)/methyl methacrylate (MMA)/ethyl acrylate (EA)/acrylic acid (AA), in the weight ratio of 45% DQS: 45% MMA: 5% EA: 56 AA, added with a polyfunctional epoxy compound (diethylene glycol diglycidyl ether, in an amount of 5% by volume based on the acrylic copolymer solid content by volume) as crosslinking agent and polyethylene imine as a crosslinking catalyst. The epoxy compound serves as a bridge formation agent for forming a bridge by reaction with the carboxylic moiety of the acrylic acid of the DQS constituent of formula Ia-1. After the above coatings were applied, dried, and hardened on surface treated polyethylene terephthalate (PET) film, the surface resistivity under normal temperature and after heating were measured.

The measured values are as follows:

Surface Resistivity

| | |
|---|---|
| 1. Under normal temperature: | $3-5 \times 10^9$ $\Omega/cm^2$ |
| 2. After heating for 60 minutes at 150° C.: | $4-6 \times 10^9$ $\Omega/cm^2$ |

Measuring environment: Temperature=20° C., Humidity= 50% RH.

Example 2

Surface resistivity under 20° C. temperature and 20% humidity was measured after adding 10% of the salt of formula Ib (instead of the salt of formula Ia) relative to the solid matter of the polymer of the coating compounds in Example 1.

Surface Resistivity

1. Coated product as per Example 2: $5.5 \times 10^9 \Omega/cm^2$
2. Coated product as per Example 1: $6.5 \times 10^9 \Omega/cm^2$ Example 3

The laminated film created by combining oriented polypropylene (OPP) film (20 microns) and polyethylene (PE) film (30 microns) using compounds which combine isocyanate type urethane adhesives with the salt of formula Ib components showed low tribostatic voltages, achieving an excellent antistatic film. Formulations and ratios of the adhesives are shown in 1) Table 1 and 2) Table 2, and the formulation ratio of the salt of formula Ib (hereinafter referred to as SSC (brand name) for convenience, and which is constituted of 100% of the chemical compound of formula Ib) relative thereto is shown in 3) Table 3, below.

TABLE 1

| 1) Formulation of the adhesive agents | | | | |
|---|---|---|---|---|
| Product Name | Type | Ingredients | Solid Matter | Solvent |
| Base | LX-783A | Aromatics Type | Polyether Polyol | 70% | Ethyl Acetate |

TABLE 1-continued

1) Formulation of the adhesive agents

| Product Name | Type | Ingredients | Solid Matter | Solvent |
| --- | --- | --- | --- | --- |
| Crosslinker KA-75 | Aromatics Type | Polyisocyanate | 75% | Ethyl Acetate |

Base: LX-783A and Crosslinker KA-75 are products made by Dai Nippon Ink Chemical Industry, Co., Ltd.

TABLE 2

2) Formulation ratio of the adhesive agents

| | Formulation Ratio | Solid Matter | Solid Weight |
| --- | --- | --- | --- |
| Base | 200 g | 70% | 140 g |
| Crosslinker | 100 g | 75% | 75 g |
| Solvent | 550 g | — | — |
| Total | 850 g | 25.29% | 215 g |

Solvent = ethyl acetate

TABLE 3

3) Formulation ratio of the salt of formula Ib (hereinafter referred to as SSC)

| Formulated Adhesive Agents | Solid Matter Ratio | Quantity of SSC Mixture | Formulation Ratio against Solid Matter |
| --- | --- | --- | --- |
| (1) 100% | 25.29% | 0 g | 0% |
| (2) 100% | 25.29% | 5 g | 18.5% |

4) Actual coating quantity of adhesive agents used: 3g/m$^2$

5) Adhesive strength of OPP/PE dry laminated film (after aging for 48 hours under 40° C. temperature):
   (1) Product formulated without SSC: LLDPE (linear low density polyethylene) breakage
   (2) Product formulated with SSC: LLDPE breakage 6) Antistatic performance of OPP/PE dry laminated film (after aging for 48 hours under 40° C. temperature):
   (1) Product formulated without SSC: surface tribostatic voltage 32.0 kv., ash attract test=present
   (2) Product formulated with SSC: surface tribostatic voltage 1.5 kv., ash attract test=absent 7) Transparency of OPP/PE dry laminated film (after aging for 48 hours under 40° C. temperature):
   (1) Product formulated without SSC: excellent transparency
   (2) Product formulated with SSC: excellent transparency Further Particulars Test formula for isocyanate type dry laminated adhesives in ethyl acetate (EtAc) as solvent:

1) Base-A—Formula for Polyester-polyol Type Polymer

| 1. M-593 (60% EtAc soln.) | 90 g (54 g solid content) |
| --- | --- |
| 2. SSC (100%) | 20 g (20 g solid content) |
| 3. EtAc | 90 g (0 g solid content) |
| Total: | 200 g (74 g, 37% solid content) |

M-593 is a polyester-polyol type polymer solution in ethyl acetate.

| AD-1 - Formula for adhesive agents | |
| --- | --- |
| 1. Base-A (37%) | 30 g (11.1 g solid content) |
| 2. CAT-56 (70%) | 7 g (4.9 g solid content) |
| 3. EtAc | 30 g (0 g solid content) |
| Total: | 67 g (16.0 g, 23.88%, solid content) |

CAT-56 is a polyisocyanate compound solution in ethyl acetate.

2) Base-B—Formula for Polyurethane-polyol Type Polymer:

| 1. TM-329 (70%) | 80 g (56 g solid content) |
| --- | --- |
| 2. SSC (100%) | 20 g (20 g solid content) |
| 3. EtAc | 106 g (0 g solid content) |
| Total: | 206 g (76 g, 36.89%, solid content) |

TM-329 is a polyurethane-polyol type polymer solution in ethyl acetate.

AD-2—Formula for Adhesive Agents

| 1. Base-B (36.89%) | 20 g (7.38 g solid content) |
| --- | --- |
| 2. CAT-8B (75%) | 20 g (15.00 g solid content) |
| 3. EtAc | 40 g (0 g solid content) |
| Total: | 80 g (22.38 g, 27.89%, solid content) |

CAT-8B is a polyisocyanate compound solution in ethyl acetate.

3) Test Results

OPP (30µ)/AD-1 (3µ)/CPP (50µ)

| 1. Adhesive strength: | film breakage 24 h after lamination |
| --- | --- |
| 2. Tribostatic voltage: surface | 0.1 kv on CPP (casted polypropylene) surface |
| | 0.2 kv on OPP surface |

OPP (30µ)/AD-2 (3µ)/CPP (50µ)

| 1. Adhesive strength: | film breakage 24 h after lamination |
| --- | --- |
| 2. Tribostatic voltage: | 0.1 kv on CPP surface |
| | 0.1 kv on OPP surface |

TM-593, TM-329, CAT-56 and CAT-8B are all polymer products manufactured by Toyo Morton Co., Ltd.

Particular Advantages of the Invention

As per below, the antistatic agents provided by the present invention possess excellent (high) antistatic performance under low ambient humidity and low temperature, and are highly effective in preventing static problems of various polymer resin products (synthetic polymer resins) under these environmental conditions. The present invention is especially effective in preventing static troubles for sublimation type thermal transfer ink ribbons.

Other applications of the present invention include:
1. Antistatic agents for urethane type ink binder
2. Antistatic agents for urethane type paint binder
3. Antistatic agents for waterproof overcoatings
4. Antistatic adhesive primer for soft polyvinyl chloride (PVC)
5. Antistatic agents for water type polystyrene (PS) ink medium
6. Modifier for obtaining antistatic isocyanate compounds
7. Antistatic urethane type anchor coat (AC) agents.

Basically, according to the invention, the quaternary ammonium salt of formula I may be used to provide a two-liquid type isocyanate system urethane bonding agent, wherein the resulting adjusted liquid formed by pre-adding the salt of formula I to the polymer resinous material is used as the two-liquid type main agent, the polymer resinous material being a polyol resin. On the other hand, the two-liquid type hardening agent may be a polyisocyanate chemical compound provided such that the terminal OH base of the quaternary ammonium salt of formula I contained in the main agent polyol resin, consequent mixing of the main agent and hardening agent, may react with the polyisocyanate of the hardening agent during their usage.

While specific embodiments of the invention have been shown and described in detail to illustrate the application of the principles of the invention, it will be understood that the invention may be embodied otherwise without departing from such principles.

What is claimed is:

1. Antistatic coating or adhesive composition comprising a polyester type resinous material which is soluble in an organic solvent, the resinous material containing a quaternary ammonium salt of formula I:

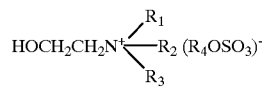
I wherein each of $R_1$, $R_2$ and $R_3$ is an alkyl radical having 1–5 carbon atoms, and $R_4$ is an alkyl radical having 1–3 carbon atoms.

2. Composition of claim 1 wherein the solvent is selected from the group consisting of ketones, esters and alcohols.

3. Composition of claim 1 wherein the quaternary ammonium salt is of formula Ia:

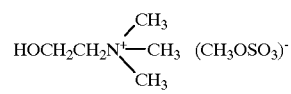
Ia

4. Composition of claim 1 wherein the quaternary ammonium salt is of formula Ib

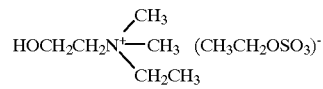
Ib

5. Method of using a quaternary ammonium salt of formula I:

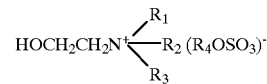
I wherein each of $R_1$, $R_2$ and $R_3$ is an alkyl radical having 1–5 carbon atoms, and $R_4$ is an alkyl radical having 1–3 carbon atoms, comprising adding the quaternary ammonium salt to a polymer type resinous material for providing an antistatic coating or adhesive composition, wherein the quaternary ammonium salt is reacted with a polyisocyanate in a polyether polyol resinous solvent.

6. Method of claim 5 wherein the quaternary ammonium salt is of formula Ia:

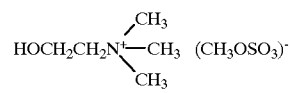
Ia

7. Method of claim 5 wherein the quaternary ammonium salt is of formula Ib:

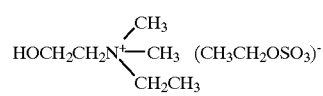
Ib

* * * * *